US010780544B2

(12) United States Patent
Twomey et al.

(10) Patent No.: US 10,780,544 B2
(45) Date of Patent: Sep. 22, 2020

(54) SYSTEMS AND METHODS FACILITATING REPROCESSING OF SURGICAL INSTRUMENTS (71) Applicant: COVIDIEN LP, Mansfield, MA (US)

(72) Inventors: John R. Twomey, Longmont, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 337 days.

(21) Appl. No.: 15/960,849

(22) Filed: Apr. 24, 2018

(65) Prior Publication Data
US 2019/0321930 A1   Oct. 24, 2019

(51) Int. Cl.
*B24B 3/36* (2006.01)
*A61B 17/32* (2006.01)
*B08B 3/08* (2006.01)
*A61B 90/70* (2016.01)
*A61B 18/14* (2006.01)
*A61B 17/00* (2006.01)

(52) U.S. Cl.
CPC .............. *B24B 3/361* (2013.01); *A61B 17/32* (2013.01); *A61B 90/70* (2016.02); *B08B 3/08* (2013.01); *A61B 18/1445* (2013.01); *A61B 2017/00526* (2013.01)

(58) Field of Classification Search
CPC ............ B24B 3/361; B24B 3/36; B24B 3/368
USPC ......................................................... 451/45
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |
| D299,413 S | 1/1989 | DeCarolis |
| 5,258,001 A | 11/1993 | Corman |
| D343,453 S | 1/1994 | Noda |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |
| 5,487,693 A * | 1/1996 | Prusaitis ................. B24B 3/605 451/45 |

(Continued)

FOREIGN PATENT DOCUMENTS

| | | |
|---|---|---|
| CN | 201299462 Y | 9/2009 |
| DE | 2415263 A1 | 10/1975 |

(Continued)

*Primary Examiner* — George B Nguyen
(74) *Attorney, Agent, or Firm* — Carter, DeLuca & Farrell LLP (57) ABSTRACT A method of sharpening a cutting edge of a knife of a surgical instrument includes manipulating an end effector assembly of a surgical instrument such that first and second jaw members of the end effector assembly are disposed in a spaced-apart position, retaining the first and second jaw members in the spaced-apart position, advancing a knife of the surgical instrument to an extended position wherein the knife extends between the first and second jaw members, retaining the knife in the extended position, and sharpening a cutting edge of the knife.

20 Claims, 6 Drawing Sheets

(56) References Cited

U.S. PATENT DOCUMENTS

| | | |
|---|---|---|
| 5,540,685 A | 7/1996 | Parins et al. |
| 5,611,808 A | 3/1997 | Hossain et al. |
| D384,413 S | 9/1997 | Zlock et al. |
| H1745 H | 8/1998 | Paraschac |
| 5,797,938 A * | 8/1998 | Paraschac ........... A61B 18/1447 606/167 |
| 5,797,941 A * | 8/1998 | Schulze ............. A61B 18/1442 606/171 |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| 7,195,631 B2 * | 3/2007 | Dumbauld ............ A61B 17/29 604/22 |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 8,020,743 B2 * | 9/2011 | Shelton, IV ..... A61B 17/07207 227/180.1 |
| D649,249 S | 11/2011 | Guerra |
| D649,643 S | 11/2011 | Allen, IV et al. |
| 8,074,859 B2 * | 12/2011 | Kostrzewski .... A61B 17/07207 227/176.1 |
| 8,257,352 B2 * | 9/2012 | Lawes ................ A61B 18/1445 606/51 |
| 8,366,709 B2 | 2/2013 | Schechter et al. |
| 8,425,504 B2 | 4/2013 | Orton et al. |
| 8,469,716 B2 | 6/2013 | Fedotov et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,663,222 B2 | 3/2014 | Anderson et al. |
| 8,679,098 B2 | 3/2014 | Hart |
| 8,685,009 B2 | 4/2014 | Chernov, et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,898,888 B2 | 12/2014 | Brandt et al. |
| 8,900,232 B2 | 12/2014 | Ourada |
| 8,906,018 B2 | 12/2014 | Rooks et al. |
| 9,585,714 B2 * | 3/2017 | Livneh .................. A61B 17/295 |
| 2008/0280540 A1 * | 11/2008 | Johnson ............. A61B 10/0275 451/45 |
| 2010/0179545 A1 | 7/2010 | Twomey et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172924 A1 | 7/2012 | Allen, IV |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0022495 A1 | 1/2013 | Allen, IV et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |

(56) References Cited

U.S. PATENT DOCUMENTS

| | | |
|---|---|---|
| 2013/0190760 A1 | 7/2013 | Allen, IV et al. |
| 2013/0197503 A1 | 8/2013 | Orszulak |
| 2013/0226178 A1 | 8/2013 | Brandt et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 10045375 C2 | 10/2002 |
| DE | 202007009165 U1 | 8/2007 |
| DE | 202007009317 U1 | 10/2007 |
| DE | 202007016233 U1 | 1/2008 |
| DE | 102004026179 B4 | 1/2009 |
| DE | 102008018406 B3 | 7/2009 |
| EP | 1159926 A3 | 3/2003 |
| JP | 61501068 | 9/1984 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | H0856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | H0910223 A | 1/1997 |
| JP | 9122138 A | 5/1997 |
| JP | H1024051 A | 1/1998 |
| JP | 10155798 A | 6/1998 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000342599 A | 12/2000 |
| JP | 2000350732 A | 12/2000 |
| JP | 2001008944 | 1/2001 |
| JP | 2001029356 A | 2/2001 |
| JP | 2001128990 A | 5/2001 |
| JP | 2001190564 A | 7/2001 |
| JP | 2001003400 | 11/2001 |
| JP | 2002528166 A | 9/2002 |
| JP | 2003245285 A | 9/2003 |
| JP | 2004517668 A | 6/2004 |
| JP | 2004528869 A | 9/2004 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 2005110264 A3 | 4/2006 |

* cited by examiner

SYSTEMS AND METHODS FACILITATING REPROCESSING OF SURGICAL INSTRUMENTS

BACKGROUND

Technical Field

The present disclosure relates to surgical instruments and, more particularly, to systems and methods facilitating reprocessing of surgical instruments.

Background of Related Art

Multi-function surgical instruments are beneficial in that they allow multiple surgical tasks to be performed with a single instrument, obviating the need to alternatingly remove and insert different instruments for performing different surgical tasks. However, in order to provide additional functionality, additional components are added that must fit within the spatial and functional constraints of the instrument. As a result, multi-function surgical instruments tend to be relatively complex in their design and manufacture.

Surgical instrument can generally be categorized as reusable instruments (e.g., instruments that are cleaned and/or sterilized), disposable instruments (e.g., instruments that are entirely discarded after a single use), and reposable instruments (e.g., instruments wherein portions are disposable and other portions are reusable after cleaning and/or sterilization). A new class of so called reprocessed instruments has recently been introduced by manufacturers. Typically, these reprocessed instruments are disposable instruments (or reposable instruments) that are collected after a surgical use and returned to a manufacturer where the instruments are disassembled, cleaned/disinfected, refurbished, re-assembled, sterilized and sold as reprocessed instruments. In many cases, most of the original parts of an instrument are re-used to provide the necessary parts for reassembly of the same instrument. Parts that wear during use, are broken during disassembly, and/or are otherwise unable to be reprocessed as-is may be refurbished, modified, and/or alternatively replaced with replacement components.

With respect to reprocessing of certain surgical instruments, such as multi-function surgical instruments, efficient and effective disassembly, cleaning/disinfection, component replacement, component refurbishment, reassembly, and sterilization can be challenging. There is therefore a need for systems and methods facilitating reprocessing of surgical instruments.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a method of sharpening a cutting edge of a knife of a surgical instrument including manipulating an end effector assembly of a surgical instrument such that first and second jaw members of the end effector assembly are disposed in a spaced-apart position, maintaining the first and second jaw members in the spaced-apart position, advancing a knife of the surgical instrument to an extended position wherein the knife extends between the first and second jaw members, retaining the knife in the extended position, and sharpening a cutting edge of the knife.

In an aspect of the present disclosure, the method further includes positioning the end effector assembly in a fixture prior to manipulating the end effector assembly.

In another aspect of the present disclosure, manipulating the end effector assembly includes operably positioning a jack between the first and second jaw members and actuating the jack to move the first and second jaw members to the spaced-apart position. The jack may further be configured to maintain the first and second jaw members in the spaced-apart position.

In still another aspect of the present disclosure, manipulating the end effector assembly includes moving the first and second jaw members to the spaced-apart position. In such aspects maintaining the first and second jaw members in the spaced-apart position includes positioning a jack between the first and second jaw members to maintain the first and second jaw members in the spaced-apart position.

In yet another aspect of the present disclosure, advancing the knife includes actuating the knife from a proximal end portion of a knife assembly including the knife. Alternatively, advancing the knife includes pulling the knife distally.

In still yet another aspect of the present disclosure, retaining the knife in the extended position includes attaching a clamp to the knife.

In another aspect of the present disclosure, the method further includes, prior to manipulating the end effector assembly, disassembling the surgical instrument such that a front end assembly including the end effector assembly and the knife is removed from a remainder of the surgical instrument.

In another aspect of the present disclosure, the method further includes, before or after sharpening the cutting edge of the knife, flushing the front end assembly, e.g., with a cleaning solution, and/or reassembling the front end assembly with the remainder of the surgical instrument.

Another method of sharpening a cutting edge of a knife of a surgical instrument provided in accordance with aspects of the present disclosure includes disassembling a surgical instrument to remove a front end assembly therefrom. The front end assembly includes an elongated shaft assembly, an end effector assembly disposed at a distal end of the elongated shaft assembly, and a knife operably disposed within the elongated shaft assembly. The method further includes manipulating the end effector assembly such that first and second jaw members of the end effector assembly are disposed in a spaced-apart position, maintaining the first and second jaw members in the spaced-apart position, advancing the knife to an extended position wherein the knife extends between the first and second jaw members, retaining the knife in the extended position, and sharpening a cutting edge of the knife.

In an aspect of the present disclosure, the method further includes positioning the end effector assembly in a fixture prior to manipulating the end effector assembly.

In another aspect of the present disclosure, manipulating the end effector assembly includes operably positioning a jack between the first and second jaw members and actuating the jack to move the first and second jaw members to the spaced-apart position.

In yet another aspect of the present disclosure, manipulating the end effector assembly includes manually moving the first and second jaw members to the spaced-apart position.

In still another aspect of the present disclosure, maintaining the first and second jaw members in the spaced-apart position includes positioning a jack between the first and second jaw members.

In still yet another aspect of the present disclosure, advancing the knife includes actuating the knife from a proximal end portion of a knife assembly including the knife. Alternatively, advancing the knife includes pulling the knife distally.

In another aspect of the present disclosure, the method further includes, before or after sharpening the cutting edge of the knife, flushing the front end assembly, e.g., with a cleaning solution, and/or reassembling the front end assembly with the surgical instrument.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
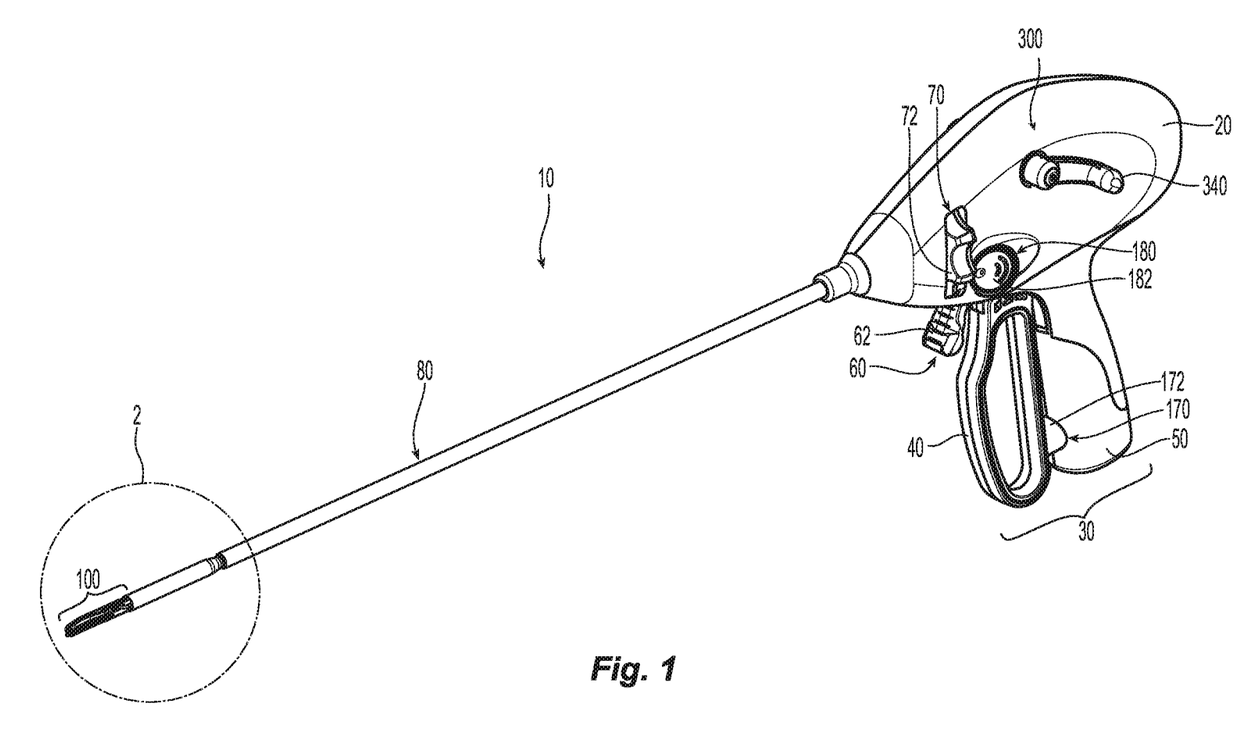
FIG. 1 is a perspective view of a multi-function surgical instrument.
Figure 2:
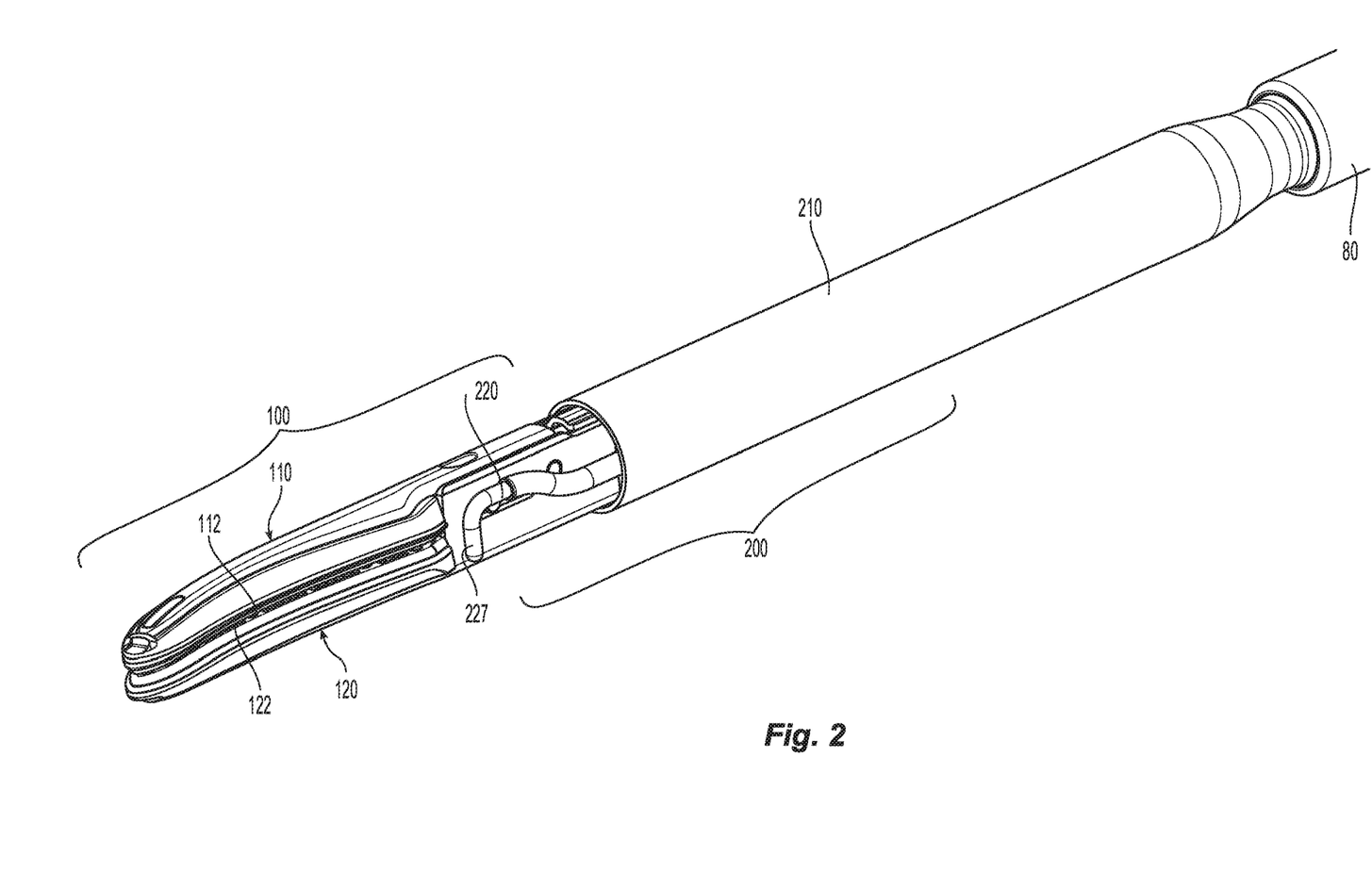
FIG. 2 is an enlarged, perspective view of a distal end portion of the surgical instrument of FIG. 1, wherein a deployable assembly thereof is disposed in a retracted position.
Figure 3:
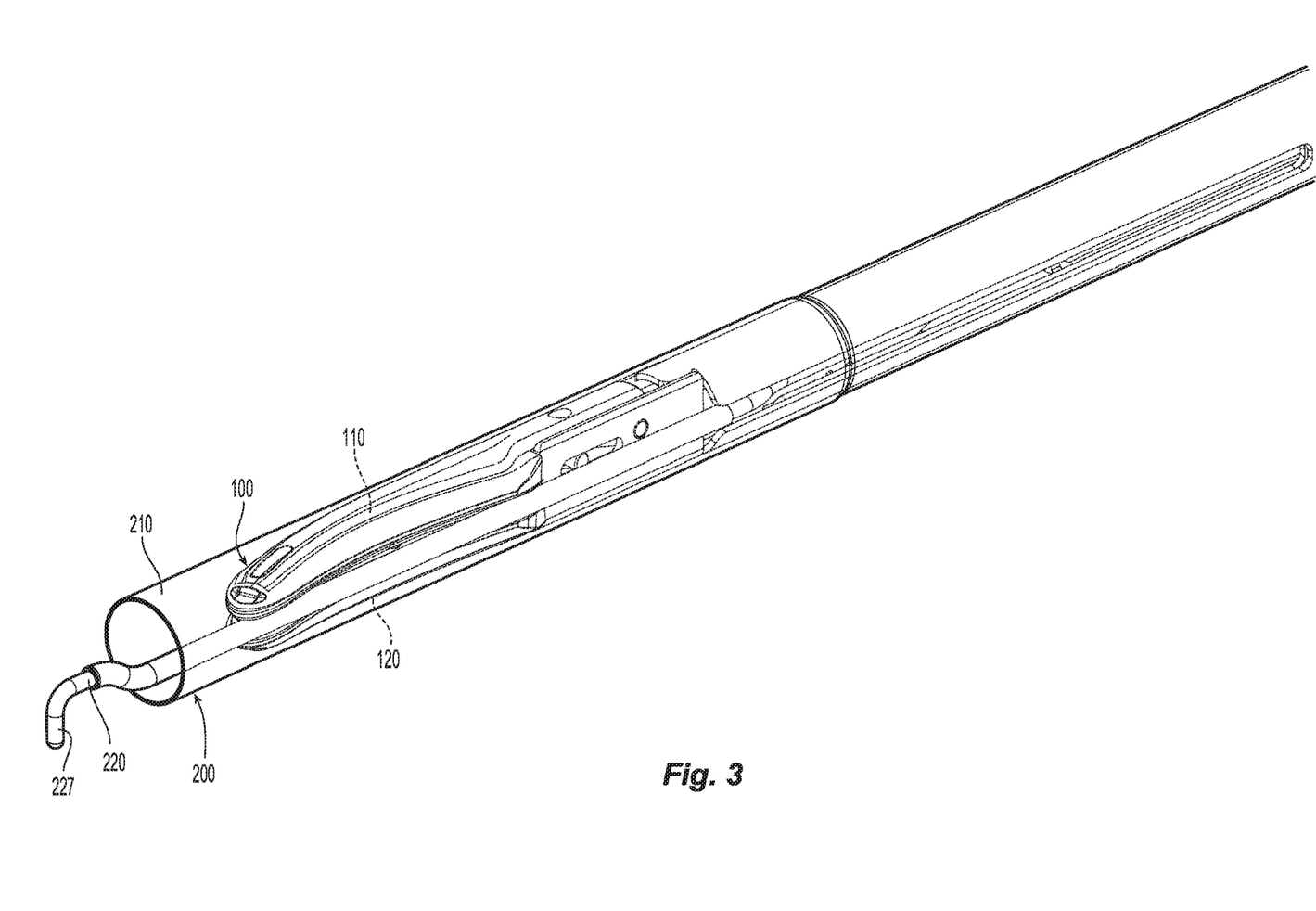
FIG. 3 is an enlarged, perspective view of the distal end portion of the surgical instrument of FIG. 1, wherein the deployable assembly is disposed in a deployed position.

Referring to FIG. 1, a multi-function surgical instrument provided in accordance with the present disclosure is shown generally identified by reference numeral 10. Instrument 10 is configured to operate in both a bipolar mode, e.g., for grasping, treating, and/or mechanically dissecting tissue, and a monopolar mode, e.g., for treating and/or electrically/electromechanically dissecting tissue. Although the present disclosure is shown and described with respect to instrument 10, the systems and methods facilitating reprocessing provided in accordance with the present disclosure are equally applicable for use with any suitable surgical instrument or portion(s) thereof. Obviously, different considerations apply to different instruments; however, the aspects and features of the present disclosure remain generally consistent regardless of the particular instrument provided. For the purposes herein, instrument 10 is generally described.

With reference to FIGS. 1-6, instrument 10 generally includes a housing 20, a handle assembly 30, a trigger assembly 60, a rotation assembly 70, an elongated shaft assembly 80, an end effector assembly 100, a drive assembly 140, a knife assembly 160, bipolar and monopolar activation assemblies 170, 180, respectively, a monopolar assembly 200, and a deployment and retraction mechanism 300. Rotation assembly 70, elongated shaft assembly 80, end effector assembly 100, drive assembly 140, knife assembly 160, and monopolar assembly 200 together form a front end assembly 400 of instrument 10 (see FIGS. 5 and 6).

Instrument 10 also includes an electrosurgical cable (not shown) that connects instrument 10 to a generator (not shown) or other suitable power source. The electrosurgical cable includes wires (not shown) extending therethrough that have sufficient length to extend through housing 20 and/or elongated shaft assembly 80 in order to provide energy to at least one of the electrically-conductive surfaces 112, 122 of jaw members 110, 120, respectively, of end effector assembly 100, e.g., upon activation of bipolar activation switch 172 of bipolar activation assembly 170 in the bipolar mode of operation. Similarly, one or more of the wires of the electrosurgical cable extends through housing 20 and/or elongated shaft assembly 80 in order to provide energy to monopolar assembly 200, e.g., upon activation of either of the monopolar activation switches 182 of monopolar activation assembly 180 in the monopolar mode of operation.

Elongated shaft assembly 80 extends distally from housing 20 and supports end effector assembly 100 at a distal end thereof. End effector assembly 100 includes opposing jaw members 110, 120 pivotably coupled to one another. Each of the jaw members 110, 120 includes an electrically-conductive surface 112, 122 adapted to connect to the source of energy and defines a bipolar configuration in use wherein surface 112 is charged to a first electrical potential and surface 122 is charged to a second, different electrical potential such that an electrical potential gradient is created for conducting energy between surfaces 112, 122 and through tissue grasped therebetween for treating tissue. Bipolar activation switch 172 of bipolar activation assembly 170 (FIG. 1) is operably coupled between the source of energy (not shown) and surfaces 112, 122 via one or more wires (not shown), thus allowing the surgeon to apply bipolar energy to surfaces 112, 122 of jaw members 110, 120, respectively, of end effector assembly 100 during a bipolar mode of operation.

Handle assembly 30 includes a movable handle 40 and a fixed handle 50. Movable handle 40 is movable relative to fixed handle 50 between an initial position, wherein movable handle 40 is spaced-apart from fixed handle 50, and a compressed position, wherein movable handle 40 is compressed towards fixed handle 50. Drive assembly 140 is operably coupled between handle assembly 30 and end effector assembly 100 such that movement of movable handle 40 between the initial position and the compressed position pivots jaw member 110 relative to jaw member 120 between the spaced-apart position and the approximated position, to a threshold force, at which point movable handle 40 is decoupled from jaw member 110 such that jaw member 110 is maintained in position despite further movement of movable handle 40 towards the compressed position. More specifically, when the threshold force is reached, a compression spring 142 (FIG. 6) of drive assembly 140 is compressed, decoupling movable handle 40 from jaw member 110 and allowing further movement of movable handle 40 towards the compressed position without impacting the position of jaw member 110. The threshold force is the force at which the drive force exceeds the spring compression force of compression spring 142. Thus, when the drive force is less than or equal to the spring compression force of compression spring 142, movement of movable handle 40 between the initial position and the compressed position pivots jaw member 110 relative to jaw member 120 between the spaced-apart position and the approximated position. On the other hand, when the drive force exceeds the spring compression force of compression spring 142, jaw member 110 is maintained in position and compression spring 142 is further compressed in response to movement movable handle 40 towards the compressed position.

Continuing with reference to FIGS. 1-4, trigger 62 of trigger assembly 60 is selectively actuatable relative to housing 20 from an un-actuated position to an actuated position. Knife assembly 160 is operably coupled to trigger 62 such that actuation of trigger 62 from the un-actuated position to the actuated position translates a knife 162 (FIGS. 7B-7D) of knife assembly 160 from a retracted position, wherein knife 162 is disposed proximally of jaw members 110, 120, to an extended position, wherein knife 162 extends at least partially between jaw members 110, 120 and through knife channels (not shown) defined within jaw members 110, 120 such that cutting edge 164 of knife 162 cuts tissue grasped between jaw members 110, 120. Movable handle 40 may include a protrusion 42 acting as a knife lockout to inhibit actuation of trigger 62 when movable handle 40 is disposed in the initial position, although other suitable knife lockouts operably coupled between trigger 62 and movable handle 40 are also contemplated.

Rotation of rotation wheel 72 of rotation assembly 70 relative to housing 20 effects corresponding rotation of at least a portion of elongated shaft assembly 80, end effector assembly 100, drive assembly 140, the knife assembly 160, and monopolar assembly 200 relative to housing 20.

Monopolar assembly 200 includes an insulative sheath 210 and an energizable member 220. Insulative sheath 210 is movable relative to end effector assembly 100 between a storage position, wherein insulative sheath 210 is disposed proximally of end effector assembly 100, and a use position, wherein insulative sheath 210 is substantially disposed about end effector assembly 100. Energizable member 220 is coupled to the source of energy (not shown) and monopolar activation assembly 180 (FIG. 1) via one or more wires (not shown) and functions as the active electrode of monopolar assembly 200. Energizable member 220 is movable together with insulative sheath 210 and relative to end effector assembly 100 between a storage position, wherein distal tissue-treating portion 227 of energizable member 220 is positioned more-proximally, and a use position, wherein distal tissue-treating portion 227 of energizable member 220 extends distally from end effector assembly 100 to facilitate treating tissue therewith. Energizable member 220, more specifically, is engaged with insulative sleeve 210 such that energizable member 220 and insulative sleeve 210 move together between their respective storage and use positions (collectively the storage and use positions of monopolar assembly 200). In the use position, insulative sheath 210 serves to electrically insulate end effector assembly 100 from distal tissue-treating portion 227 of energizable member 220, while distal tissue-treating portion 227 extends distally from end effector assembly 100. In the use position, energy may be supplied to distal tissue-treating portion 227 of energizable member 220, e.g., via activation of either of the activation switches 182 of monopolar activation assembly 180 (FIG. 1), for treating tissue in the monopolar mode of operation.

Deployment and retraction mechanism 300 is configured for selectively transitioning monopolar assembly 200 between its storage condition and its use condition. Deployment and retraction mechanism 300 generally includes a gear box 310 mounted within housing 20, a gear assembly 320 operably disposed within gear box 310, a pair of input shafts 330 operably coupled to gear assembly 320 and extending transversely from either side of gear box 310 and outwardly from housing 20 through apertures defined through housing 20, a pair of deployment paddles 340 operably coupled to the input shafts 330, and a slider 360 disposed within housing 20 and operably coupling an output of gear assembly 330 with energizable member 220 of monopolar assembly 200 (which, in turn, is engaged with insulative sleeve 210) such that deployment and retraction mechanism 300 is configured to enable both deployment and retraction of monopolar assembly 200 in a push-push manner, e.g., wherein monopolar assembly 200 is both deployed and retracted by pushing either of paddles 340 in the same direction.

Figure 4:
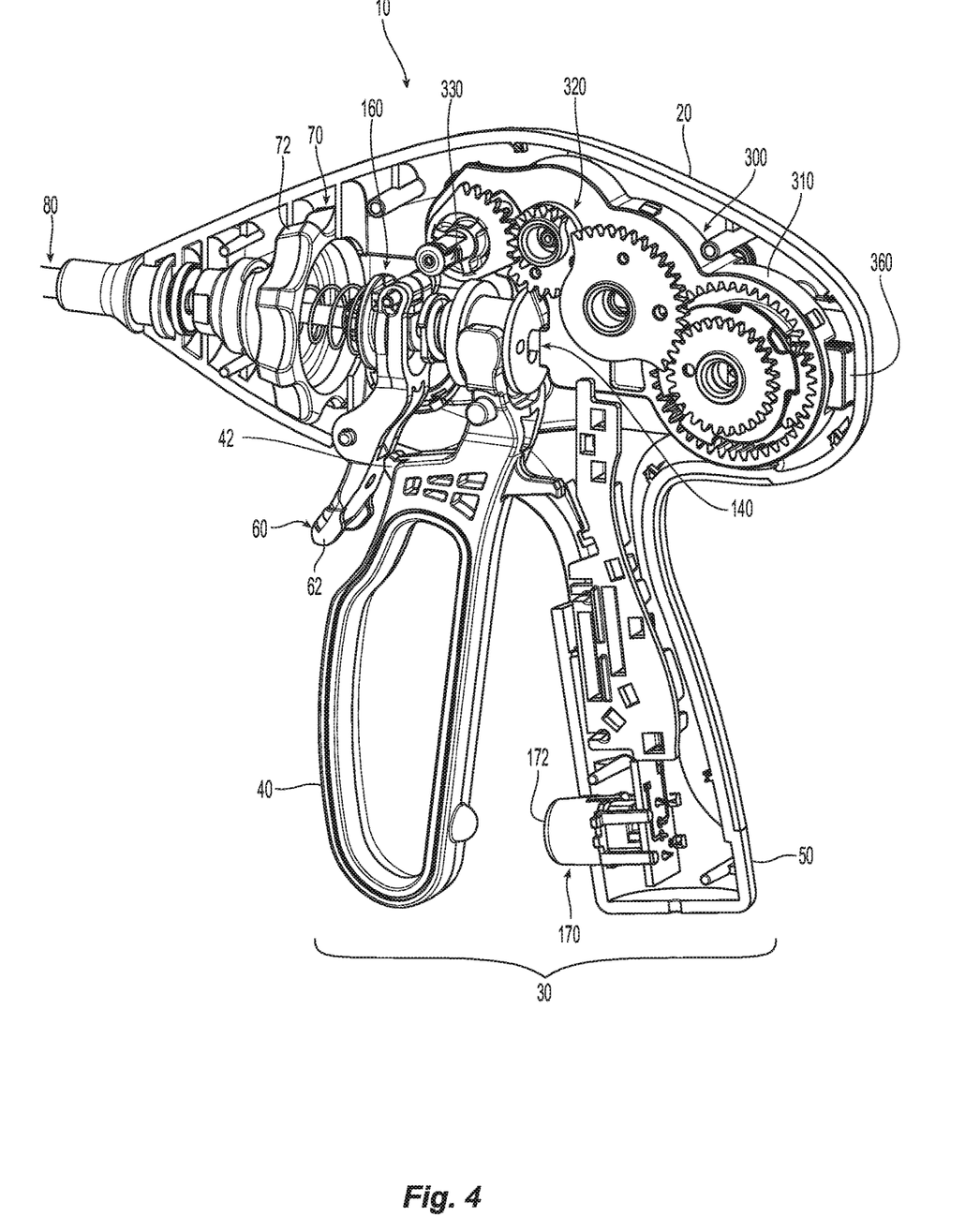
FIG. 4 is a perspective view of a proximal end portion of the surgical instrument of FIG. 1 with portions removed to illustrate the internal working components thereof.
Figure 5:
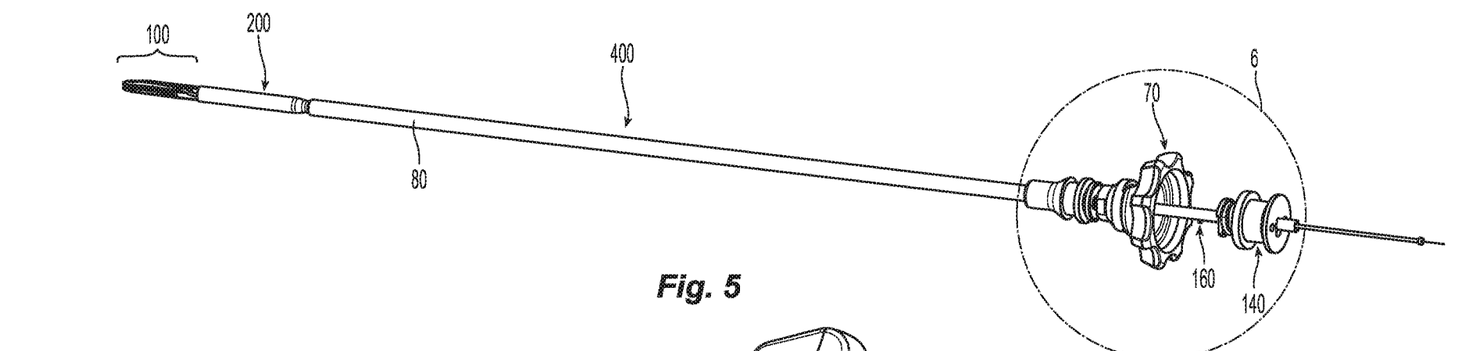
FIG. 5 is a perspective view of a front end assembly of the surgical instrument of FIG. 1, with portions thereof removed.
Figure 6:
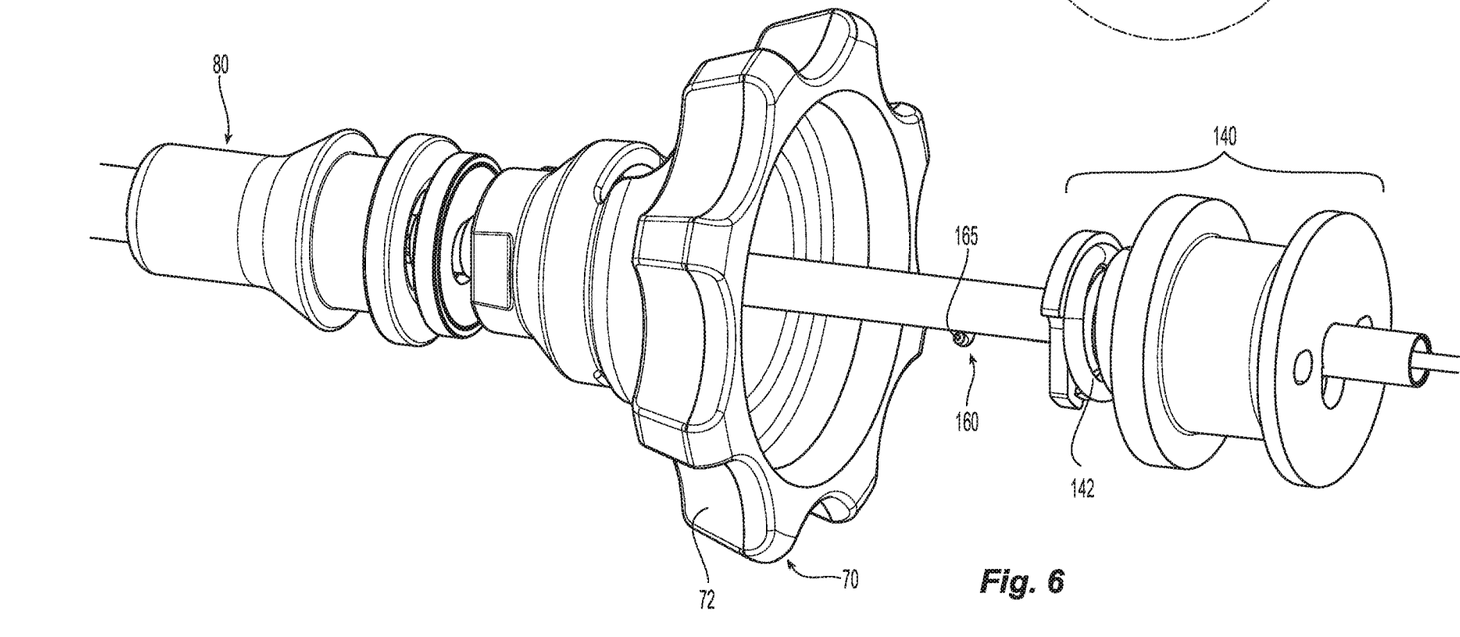
FIG. 6 is an enlarged, perspective view of the area of detail indicated as "6" in FIG. 5.

Referring to FIGS. 4-6, with regard to the disassembly, cleaning/disinfection, re-assembly, and sterilization of instrument 10 during reprocessing, the various components and assemblies of instrument 10 and the arrangement thereof make disassembling and re-assembling time consuming and challenging. Therefore, avoiding the need to disassemble portions of instrument 10 is advantageous, assuming the components of these portions to remain in-tact can be readily reconditioned and sterilized for reuse. With respect to knife 162 (FIGS. 7B-7D), for example, it has been found that cutting edge 164 may dull during use, thus requiring sharpening as part of reprocessing instrument 10. Provided below are systems and methods enabling sharpening of cutting edge 164 of knife 162 without requiring disassembly of front end assembly 400 of instrument 10. As such, the disassembly and re-assembly of front end assembly 400 during reprocessing is obviated.

In order to reprocess instrument 10, in embodiments, paddles 340 of deployment and retraction mechanism 300 (FIG. 1) are removed, housing 20 is opened, and the various components therein are removed. More specifically, the various components coupled to front end assembly 400 may be decoupled therefrom to enable front end assembly 400 to be removed as a unit. With front end assembly 400 removed from instrument 10, cutting edge 164 of knife 162 may be sharpened, as detailed below, without disassembly of front end assembly 400. In embodiments, instead of separating front end assembly 400 from instrument 10, cutting edge 164 of knife 162 may be sharpened similarly as detailed below while instrument 10 is fully in-tact or partially disassembled (with front end assembly 400 still assembled therewith).

Figure 7A:
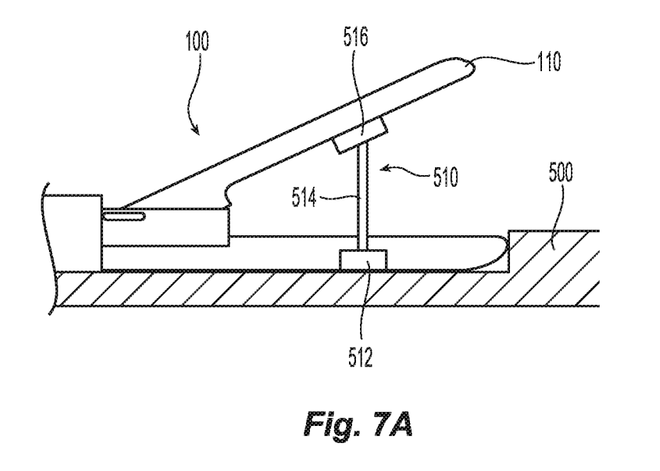
FIGS. 7A-7D are side views of a distal end portion of the front end assembly of FIG. 5 illustrating systems and methods for sharpening the knife thereof without requiring disassembly of the front end assembly.

Turning to FIGS. 7A-7D, and with initial reference to FIG. 7A, in order to sharpen cutting edge 164 of knife 162 without removing knife 162 from front end assembly 400, front end assembly 400, or at least end effector assembly 100 thereof, is placed in a fixture 500 to retain end effector assembly 100 in position. Thereafter, jaw members 110, 120 of end effector assembly 100 are moved to the spaced-apart position and a jack 510 is positioned to maintain jaw members 110, 120 in the spaced-apart position. Jack 510 may include a base 512 engaged with or otherwise disposed on fixture 500, a shaft 514 extending from base 512, and a support 516 disposed at the opposite end of shaft 514 for abutting jaw member 110 to maintain jaw member 110 in the spaced-apart position. Jack 510 may be a stationary fixture or an adjustable fixture. Jaw members 110, 120 may be manually opened and jack 510 thereafter positioned to maintain jaw members 110, 120 in the spaced-apart position, or support 516 of jack 510 may be positioned between jaw members 110, 120 and jack 510 thereafter actuated (in embodiments where jack 510 is adjustable) to elongate shaft 514 to urge jaw member 110 to pivot relative to jaw member 120 to the spaced-apart position, similar to a car jack. In the former embodiments, jack 510 need not be adjustable and may instead simply be a support structure for maintaining jaw members 110, 120 in the spaced-apart position. Other configurations are also contemplated.

Figure 7B:
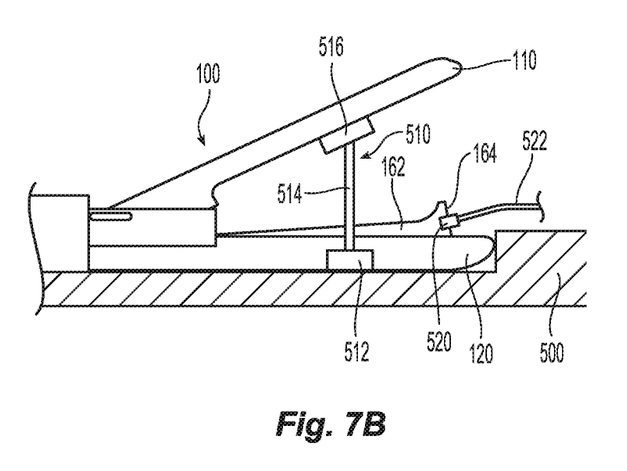

Referring to FIG. 7B, with fixture 500 retaining end effector assembly 100 and jack 510 maintaining jaw member 110 in the spaced-apart position, knife 162 is moved to the extended position. Knife 162 may be moved to the extended position using a grasping device 520 coupled to a pull wire 522, as shown, may be moved to the extended position by manipulating knife assembly 160 at the proximal end 165 thereof (see FIG. 6), or may be moved to the extended position in any other suitable manner.

Figure 7C:
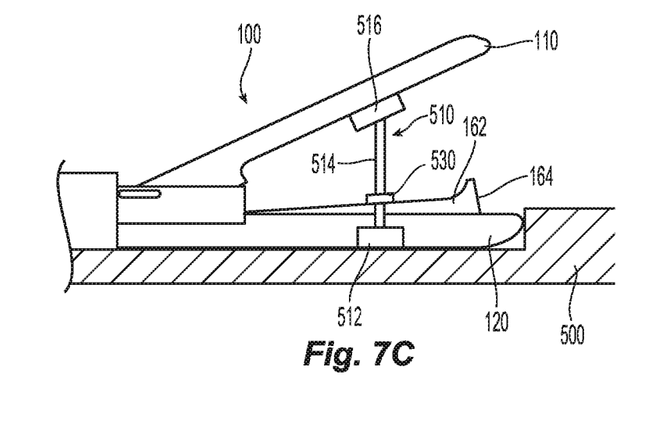

With reference to FIG. 7C, once knife 162 is moved to the extended position, a clamp 530 may be engaged with knife 162 at a position proximally-spaced from cutting edge 164. Clamp 530 may also be engaged with shaft 514 of jack 510, as shown, fixture 500, or any other suitable component to maintain knife 162 in the extended position.

Figure 7D:
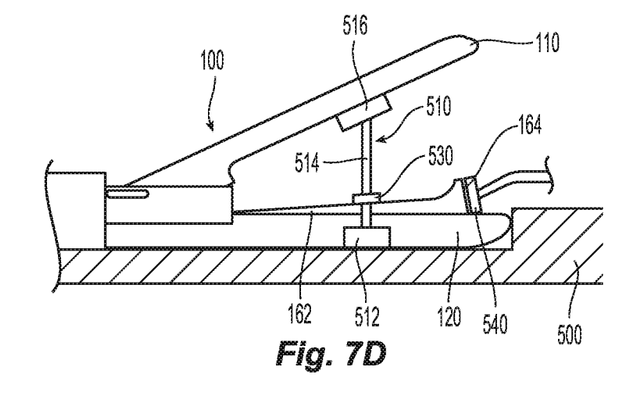

Turning to FIG. 7D, with end effector assembly 100 retained, jaw members 110, 120 disposed in the spaced-apart position, and knife 162 held in the extended position, a knife sharpener 540 may be moved into position to sharpen cutting edge 164 of knife 162. Knife sharpener 540 may be a jig-assisted sharpener, sharpening stone-based sharpener, push-through sharpener, grinder sharpener, belt sharpener, or other suitable knife sharpener and may be manually operated or powered.

Referring again to FIGS. 7A-7D, once cutting edge 164 of knife 162 is sufficiently sharpened, clamp 530 and jack 510 are removed and end effector assembly 100 withdrawn from fixture 500. Thereafter, front end assembly 400 may be flushed with a suitable fluid, e.g., a cleaning solution, to clean front end assembly 400 and remove any debris from the sharpening process. In embodiments, front end assembly 400 may additionally or alternatively be flushed with a suitable fluid, e.g., a cleaning solution, prior to sharpening knife 162 to rid any tissue, blood, and/or other debris accumulated during the previous surgical use, before the sharpening process is performed as detailed above. Front end assembly 400 may further be cleaned, refurbished, and/or otherwise reprocessed, before being re-assembled into instrument 10 and sterilized.

Referring generally to FIGS. 1-7D, in embodiments, sharpening of cutting edge 164 of knife 162 is effected without requiring disassembly of front end assembly 400 from housing 20, handle assembly 30, or trigger assembly 60 and, in embodiments, without requiring any disassembly (or minimal disassembly) of instrument 10. In such embodiments, instrument 10 is placed in fixture 500 to retain end effector assembly 100 in position and movable handle 40 is moved to the initial position to move jaw members 110, 120 of end effector assembly 100 to the spaced-apart position. Thereafter, jack 510 is positioned to maintain jaw members 110, 120 in the spaced-apart position. Next, movable handle 40 is moved to the compressed position or sufficiently to the compressed position such that the knife lockout, e.g., protrusion 42, is cleared and, thus, trigger 62 may be actuated to advance knife 162 to the extended position. More specifically, with jack 510 maintaining jaw members 110, 120 in the spaced-apart position, movable handle 40 is moved towards the compressed position with sufficient force to reach the threshold force such that compression spring 142 (FIG. 6) is compressed, thus allowing movement of movable handle 40 towards the compressed position without impacting the position of jaw members 110, 120 which, as noted above, are maintained in the spaced-apart position via jack 510. Movable handle 40 is maintained, e.g., manually held, latched (with a separate latching device or, in embodiments where so provided, a latch incorporated into instrument 10), or otherwise retained, in the compressed or sufficiently compressed position so as to maintain the knife lockout in a disengaged state.

Next, trigger 62 is actuated (which is permitted, despite jaw members 110, 120 being in the spaced-apart position, since the knife lockout has been cleared, as detailed above), to advance knife 162 to the extended position. Knife 162 may be maintained in the extended position via manually holding trigger 62 in the actuated position, latching (with a separate latching device), otherwise retaining trigger 62, or by holding knife 162, similarly as detailed above. Thereafter, cutting edge 164 of knife 162 may be sharpened similarly as detailed above.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of sharpening a cutting edge of a knife of a surgical instrument, comprising:
   manipulating an end effector assembly of a surgical instrument such that first and second jaw members of the end effector assembly are disposed in a spaced-apart position;
   maintaining the first and second jaw members in the spaced-apart position;
   advancing a knife of the surgical instrument to an extended position wherein the knife extends between the first and second jaw members;
   retaining the knife in the extended position; and
   sharpening a cutting edge of the knife.

2. The method according to claim 1, further comprising positioning the end effector assembly in a fixture prior to manipulating the end effector assembly.

3. The method according to claim 1, wherein manipulating the end effector assembly includes operably positioning a jack between the first and second jaw members and actuating the jack to move the first and second jaw members to the spaced-apart position.

4. The method according to claim 3, wherein the jack is configured to maintain the first and second jaw members in the spaced-apart position.

5. The method according to claim 1, wherein manipulating the end effector assembly includes moving the first and second jaw members to the spaced-apart position, and wherein maintaining the first and second jaw members in the spaced-apart position includes positioning a jack between the first and second jaw members to maintain the first and second jaw members in the spaced-apart position.

6. The method according to claim 1, wherein advancing the knife includes actuating the knife from a proximal end portion of a knife assembly including the knife.

7. The method according to claim 1, wherein advancing the knife includes pulling the knife distally.

8. The method according to claim 1, wherein retaining the knife in the extended position includes attaching a clamp to the knife.

9. The method according to claim 1, further comprising, prior to manipulating the end effector assembly, disassembling the surgical instrument such that a front end assembly including the end effector assembly and the knife is removed from a remainder of the surgical instrument.

10. The method according to claim 9, further comprising flushing the front end assembly with a cleaning solution before and/or after sharpening the cutting edge of the knife.

11. The method according to claim 10, further comprising reassembling the front end assembly with the remainder of the surgical instrument.

12. A method of sharpening a cutting edge of a knife of a surgical instrument, comprising:
   disassembling a surgical instrument to remove a front end assembly therefrom, the front end assembly including an elongated shaft assembly, an end effector assembly disposed at a distal end of the elongated shaft assembly, and a knife operably disposed within the elongated shaft assembly;
   manipulating the end effector assembly such that first and second jaw members of the end effector assembly are disposed in a spaced-apart position;
   maintaining the first and second jaw members in the spaced-apart position;
   advancing the knife to an extended position wherein the knife extends between the first and second jaw members;
   retaining the knife in the extended position; and
   sharpening a cutting edge of the knife.

13. The method according to claim 12, further comprising positioning the end effector assembly in a fixture prior to manipulating the end effector assembly.

14. The method according to claim 12, wherein manipulating the end effector assembly includes operably positioning a jack between the first and second jaw members and actuating the jack to move the first and second jaw members to the spaced-apart position.

15. The method according to claim 12, wherein manipulating the end effector assembly includes manually moving the first and second jaw members to the spaced-apart position.

16. The method according to claim 12, wherein maintaining the first and second jaw members in the spaced-apart position includes positioning a jack between the first and second jaw members.

17. The method according to claim 12, wherein advancing the knife includes actuating the knife from a proximal end portion of a knife assembly including the knife.

18. The method according to claim 12, wherein advancing the knife includes pulling the knife distally.

19. The method according to claim 12, further comprising flushing the front end assembly with a cleaning solution before and/or after sharpening the cutting edge of the knife.

20. The method according to claim 12, further comprising reassembling the front end assembly with the surgical instrument.

* * * * *